United States Patent
Macke et al.

(10) Patent No.: US 10,238,402 B2
(45) Date of Patent: Mar. 26, 2019

(54) SURGICAL BONE RASP HAVING FLATTENED MEDIAL TEETH

(71) Applicant: Zimmer, Inc., Warsaw, IN (US)

(72) Inventors: Jacob Macke, Warsaw, IN (US);
Daniela Casanova, Dinhard (CH);
David L. Glass, Silver Lake, IN (US);
Christopher J. Holt, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 321 days.

(21) Appl. No.: 14/909,822

(22) PCT Filed: Jul. 2, 2014

(86) PCT No.: PCT/US2014/045219
§ 371 (c)(1),
(2) Date: Feb. 3, 2016

(87) PCT Pub. No.: WO2015/020743
PCT Pub. Date: Feb. 12, 2015

(65) Prior Publication Data
US 2016/0302803 A1    Oct. 20, 2016

Related U.S. Application Data

(60) Provisional application No. 61/864,033, filed on Aug. 9, 2013.

(51) Int. Cl.
*A61B 17/16* (2006.01)

(52) U.S. Cl.
CPC ...... *A61B 17/1659* (2013.01); *A61B 17/1668* (2013.01)

(58) Field of Classification Search
CPC .................. A61B 17/1668; A61B 17/1659
See application file for complete search history.

(56) References Cited

U.S. PATENT DOCUMENTS

| 3,815,599 A | 6/1974 | Deyerle |
| 4,552,136 A | 11/1985 | Kenna |

(Continued)

FOREIGN PATENT DOCUMENTS

WO    WO-2015020743 A1    2/2015

OTHER PUBLICATIONS

"International Application Serial No. PCT/US2014/045219, International Search Report dated Sep. 8, 2014", 3 pgs.

(Continued)

*Primary Examiner* — Olivia C Chang
(74) *Attorney, Agent, or Firm* — Schwegman Lundberg & Woessner, P.A.

(57) ABSTRACT

A surgical bone rasp includes a body having posterior, anterior, medial, and lateral surfaces. The medial surface includes a proximal curved portion shaped to extend substantially along a concave medial curve. The proximal curved portion includes a plurality of teeth. Each tooth in the plurality includes a tooth gullet wall, a tooth undercut, and a tooth land between the proximal and tooth undercuts. The tooth lands can be generally flat and can extend along the concave medial curve. The tooth gullet walls can be parallel to one another and can be angled to extend away from the body between a distal direction and a medial direction. The tooth undercuts can be parallel to one another, can be angled to extend away from the body in a medial direction, and can be equally spaced apart along the longitudinal axis.

17 Claims, 3 Drawing Sheets

(56) References Cited

U.S. PATENT DOCUMENTS

| | | | |
|---|---|---|---|
| 4,671,275 A | | 6/1987 | Deyerle |
| 4,944,763 A | * | 7/1990 | Willert ............... A61F 2/30771 623/23.29 |
| 5,041,118 A | | 8/1991 | Wasilewski |
| 5,454,815 A | * | 10/1995 | Geisser .............. A61B 17/1659 606/79 |
| 5,665,091 A | * | 9/1997 | Noble ................ A61B 17/1659 606/79 |
| 6,319,256 B1 | * | 11/2001 | Spotorno ........... A61B 17/1659 606/79 |
| 2004/0138756 A1 | * | 7/2004 | Reeder .................. A61B 17/15 623/21.11 |
| 2010/0023014 A1 | * | 1/2010 | Romagnoli ........ A61B 17/1659 606/85 |
| 2012/0245646 A1 | * | 9/2012 | Gustilo ................ A61B 17/164 606/86 R |
| 2013/0144350 A1 | | 6/2013 | Yoko et al. |

OTHER PUBLICATIONS

"International Application Serial No. PCT/US2014/045219, Written Opinion dated Sep. 8, 2014", 5 pgs.

"European Application Serial No. 14742428.7, Communication Pursuant to Article 94(3) EPC dated Nov. 24, 2017", 5 pgs.

"International Application Serial No. PCT/US2014/045219, International Preliminary Report on Patentability dated Feb. 18, 2016", 7 pgs.

"European Application Serial No. 14742428.7, Response filed Oct. 10, 2016 to Communication pursuant to Rules 161(1) and 162 EPC dated Mar. 31, 2016", 11 pgs.

"European Application Serial No. 14742428.7, Response filed Mar. 23, 2018 to Communication Pursuant to Article 94(3) EPC dated Nov. 24, 2017", 22 pgs.

\* cited by examiner

SURGICAL BONE RASP HAVING FLATTENED MEDIAL TEETH

CLAIM OF PRIORITY

This application is a U.S. National Stage Application under 35 U.S.C. 371 from International Application No. PCT/US2014/045219, filed Jul. 2, 2014, and published as WO 2015/020743, which claims the benefit of U.S. Provisional Patent Application Ser. No. 61/864,033, filed on Aug. 9, 2013, the benefit of priority of each of which is claimed hereby, and which are incorporated by reference herein in their entirety.

BACKGROUND

In some types of surgical procedures, a practitioner implants a prosthesis component into an elongated canal within a bone. For instance, in hip replacement surgery, a practitioner forms a canal originating at the proximal end of a femur and extending into the femur a predetermined distance, then implants a prosthesis component into the canal. In order to obtain a proper fit for the implanted component, the bone canal should be sized and shaped properly.

A practitioner can use a surgical bone rasp to form a canal within a femur. The bone rasp can include teeth or other abrasive elements on one or more exterior surfaces. The practitioner uses the rasp to cut or scrape away bone in the canal, until the canal is suitably sized and shaped to match a prosthesis component to be implanted. In many cases, the practitioner strikes a proximal end of the bone rasp with a hammer.

OVERVIEW

A surgical bone rasp includes a body having posterior, anterior, medial, and lateral surfaces. The medial surface includes a proximal curved portion shaped to extend substantially along a concave medial curve. The proximal curved portion includes a plurality of teeth. Each tooth in the plurality includes a tooth gullet wall, a tooth undercut, and a tooth land between the proximal and tooth undercuts. The tooth lands can be generally flat and can extend along the concave medial curve. The tooth gullet walls can be parallel to one another and can be angled to extend away from the body between a distal direction and a medial direction. The tooth undercuts can be parallel to one another, can be angled to extend away from the body in a medial direction, and can be equally spaced apart along the longitudinal axis.

There are potential advantages to shaping and locating the rasp teeth as noted above and further noted below. For instance, when shaped and located as noted, the rasp teeth can be used to redirect the rasp within a bone canal. The flattened teeth can allow the rasp to push off the bone, rather than dig into the bone. When the rasp is struck at its proximal end, the flattened teeth can ride along the bone and can push the rasp in an opposing direction within the bone. This redirection of the rasp can be desirable for a practitioner. In contrast to a rasp that uses sharp teeth, the present rasp including flattened teeth can have a reduced probability of getting stuck by digging into hard medial bone, such as cortical bone, before the rasp has reached a proper alignment in the bone. In contrast to a rasp that uses no teeth, the present rasp can remove less hard bone, such as cancellous bone, to achieve the proper canal size in the bone.

This Overview is intended to provide examples of the present patent document. It is not intended to provide an exclusive or exhaustive explanation of the invention. The Detailed Description below is included to provide further information about the present surgical bone rasp and the corresponding methods.

BRIEF DESCRIPTION OF THE DRAWINGS

In the drawings, which are not necessarily drawn to scale, like numerals describe similar components in different views. The drawings illustrate generally, by way of example, but not by way of limitation, various embodiments discussed in the present patent document.

DETAILED DESCRIPTION

The notations of proximal, distal, lateral, medial, anterior, and posterior are used below to describe a bone rasp and its associated elements. These notations are used for convenience, and are used to describe locations on the rasp when the rasp is being used by a practitioner during surgery. These notations also describe the rasp when the rasp is not in use. For instance, the distal tip of the rasp describes the tip of the rasp that is most distal while the rasp is in use; the description of the distal tip also applies to the same region on the rasp even when the rasp is not in use or in storage.

Figure 1:
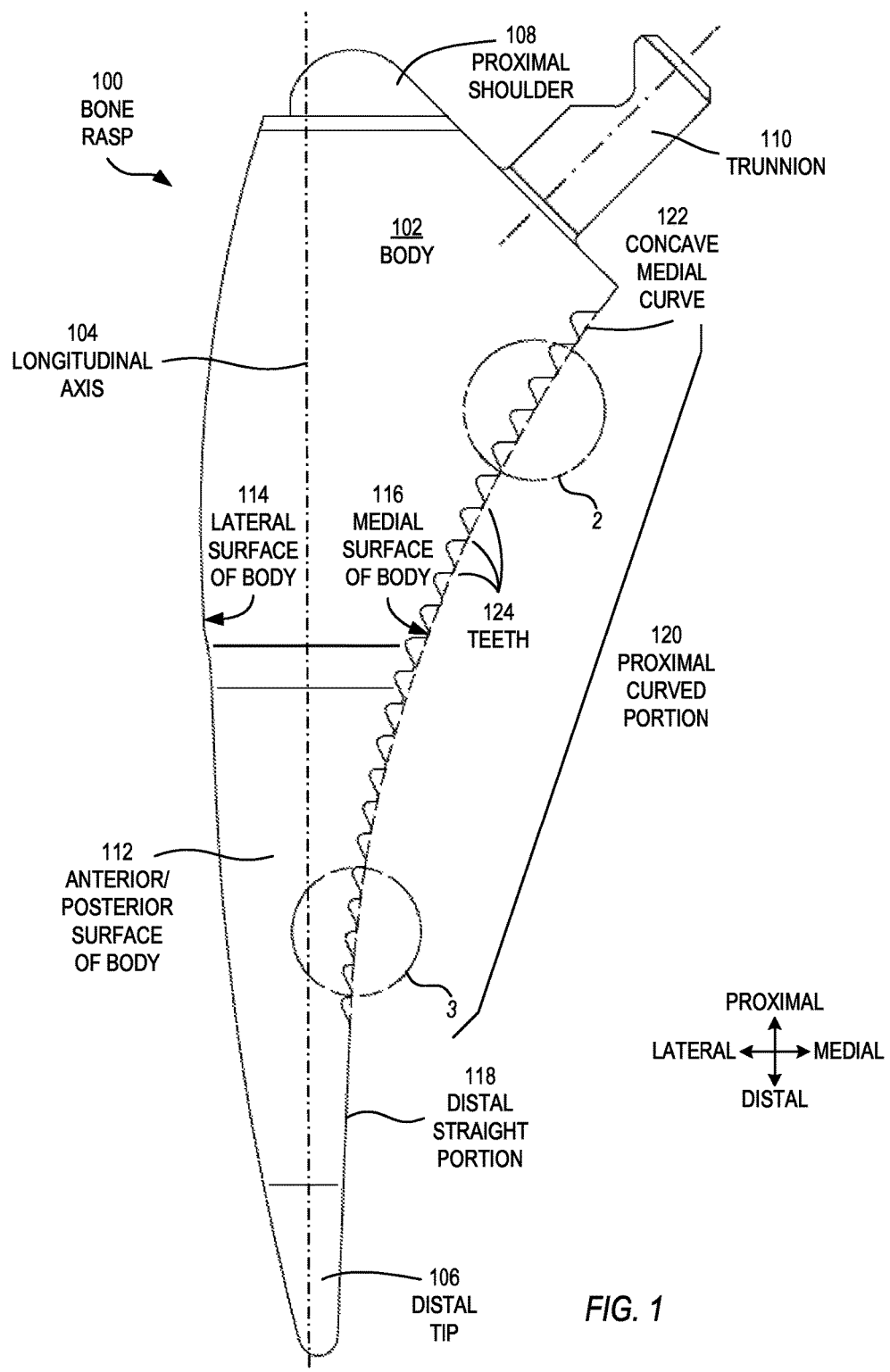
FIG. 1 is a coronal plane-view drawing of an example of a bone rasp.

FIG. 1 is a coronal plane-view drawing of an example of a bone rasp 100. The bone rasp of FIG. 1 is used for hip replacement surgery; other rasp configurations can be used for other suitable surgical procedures.

The bone rasp 100 includes a body 102. The body 102 is elongated along a longitudinal axis 104. The longitudinal axis 104 is aligned with a proximal-distal direction. The body 102 includes a distal tip 106, a proximal shoulder 108, and a trunnion 110.

The bone rasp 100 is symmetric about the coronal plane, so that the same rasp may be used for a left hip replacement or a right hip replacement. Because of this symmetry, element 112 is either a posterior surface of the body 102 for a left hip procedure, or an anterior surface of the body 102 for a right hip procedure. The surface of the body 102 opposite element 112 (i.e., facing away from the viewer in FIG. 1) is either an anterior surface of the body 102 for a left hip procedure, or a posterior surface of the body 102 for a right hip procedure.

Both the posterior and anterior surfaces 112 of the body 102 can be flat. Both the posterior and anterior surfaces 112 of the body 102 can be parallel to each other and the longitudinal axis 104, or can be angled with respect to each other and narrowing toward the distal tip 106. Alternatively, either or both of the posterior and anterior surfaces of the body 102 can be curved. The curvature can be convex or concave, and can include different curvatures at different locations on the posterior and anterior surfaces. The posterior and/or anterior surfaces 112 can include teeth with generally flat tooth lands, which are not shown in FIG. 1.

A lateral surface 114 of the body 102 is convexly curved between the distal tip 106 and the proximal shoulder 108. Alternatively, the lateral surface 114 can include one or more regions that are flat or have concave curvature. The lateral surface 114 can include teeth, which are not shown in FIG. 1.

A medial surface 116 of the body 102 includes a distal straight portion 118, which extends proximally from the distal tip 106. In some examples, the distal straight portion 118 is flat. In other examples, the distal straight portion 118 can include a slight convex curvature, with the curvature being around an axis parallel to the longitudinal axis 104. In still other examples, the distal straight portion 118 can be flat in its central portion, with a convex curvature or a bevel at its anterior and posterior edges. The distal straight portion 118 can include teeth, which are not shown in FIG. 1.

The medial surface 116 further includes a proximal curved portion 120, which extends proximally from the distal straight portion 118. The proximal curved portion 120 is tangent to the distal straight portion 118 at the point at which they adjoin. The proximal curved portion 120 is shaped to extend substantially along a concave medial curve 122.

The proximal curved portion 120 includes a plurality of medial teeth 124 thereon. Cutout regions 2 and 3, which are expanded in FIGS. 2 and 3, show further detail of a proximal series of medial teeth 124 and a distal series of medial teeth 124, respectively.

Figure 2:
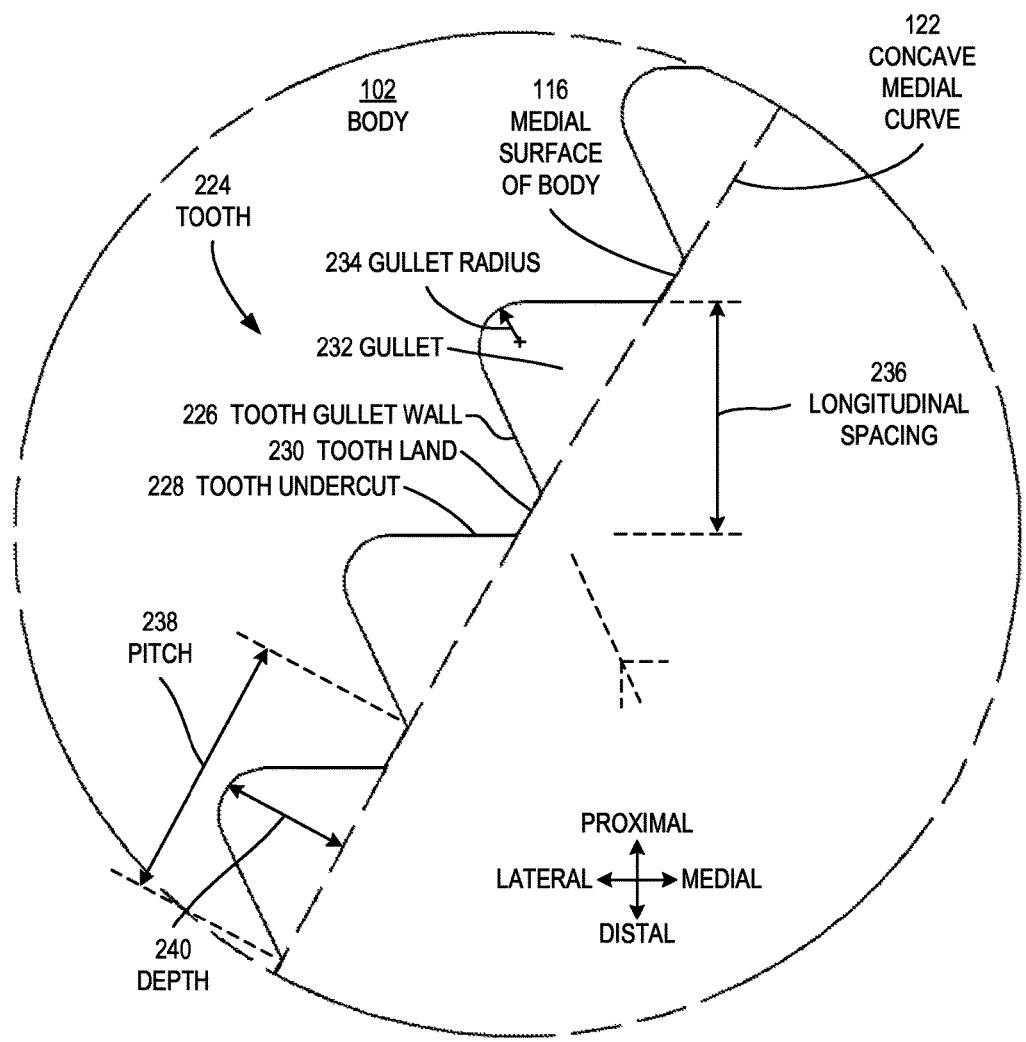
FIG. 2 is a close-up view of a proximal series of medial teeth on the bone rasp of FIG. 1.
Figure 3:
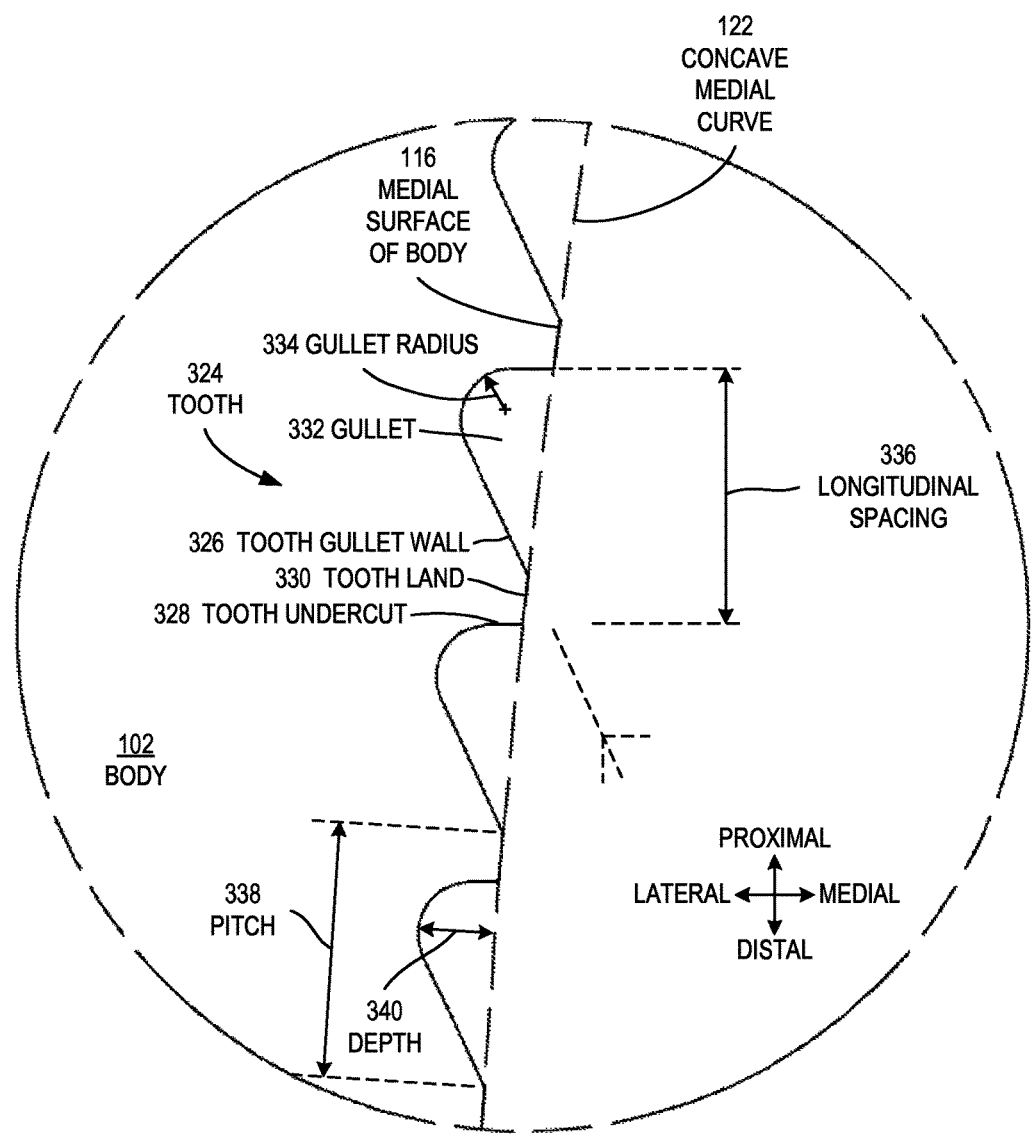
FIG. 3 is a close-up view of a distal series of medial teeth on the bone rasp of FIG. 1.

FIG. 2 is a close-up view of a proximal series of teeth 224 on the medial surface 116 of the body 102 of the bone rasp of FIG. 1. The teeth 224 are all formed similarly in construction, with element properties that change gradually from the proximal end of the proximal curved portion of the medial surface 116 of the body 102 to the distal end of the proximal curved portion of the medial surface 116 of the body 102.

Each tooth 224 includes a tooth gullet wall 226. In some examples, the tooth gullet walls 226 of the teeth 224 are parallel to one another. In some of these examples, the tooth gullet walls 226 of the teeth 224 are angled to extend away from the body 202 between a distal direction and a medial direction. In other examples, at least one tooth gullet wall 226 is not parallel to at least one other tooth gullet wall 226.

Each tooth 224 includes a tooth undercut 228. In some examples, the tooth undercuts 228 of the teeth 224 are parallel to one another. In some of these examples, the tooth undercuts 228 of the teeth 224 are angled to extend away from the body 102 in a medial direction. In other examples, at least one tooth undercut 228 is not parallel to at least one other tooth undercut 228.

Each tooth 224 includes a tooth land 230 between the proximal 226 and distal 228 walls. In some examples, the tooth lands 230 are generally flat. In some examples, the tooth lands 230 are generally parallel to the concave medial curve 122. Here, the term generally is intended to allow the tooth lands 230 to deviate slightly from true flatness, in order to allow the tooth lands 230 to follow the concave medial curve 122. The term generally is also intended to allow the tooth lands 230 to deviate slightly from the concave medial curve 122, in order to allow each tooth land 230 to be truly flat or to include a small amount of curvature that does not correspond to the curvature of the concave medial curve 122. In some examples, the tooth lands 230 extend, or extend generally, along the concave medial curve 122. The tooth lands 230 can include small bevels or rounded edges at the intersections with the tooth gullet walls 226 and the tooth undercuts 228.

Each pair of adjacent teeth 224 can have a gullet 232 therebetween. Each gullet 232 can be concave with a gullet radius 234. In some examples, the gullet radii 234 are all the same. In other examples, at least two of the gullet radii 234 are different.

The teeth 224 can be spaced apart such that the tooth undercuts 228 have a longitudinal spacing 236, taken along the longitudinal axis, between adjacent undercuts 228. In some examples, the longitudinal spacing 236 is the same for all teeth 224. In other examples, the longitudinal spacing 236 varies from tooth-to-tooth.

The tooth spacing, in a direction parallel to the concave medial curve 122, is referred to as the pitch 238. In some examples, the pitches 238 increase gradually, from a distal end of the proximal curved portion 120 to a proximal end of the proximal curved portion 120.

Each tooth 224 has a respective depth 240. The depth 240 is defined as the distance from the deepest point of the gullet 232 to the concave medial curve 122, measured in a direction perpendicular to the concave medial curve 122. In some examples, the tooth depths decrease gradually, from the proximal portion of the proximal curved portion 120, as shown in FIG. 2, to a distal portion of the proximal curved portion 120, as shown in FIG. 3.

FIG. 3 is a close-up view of a distal series of teeth 324 on the medial surface 116 of the body 102 of the bone rasp of FIG. 1. The teeth 324 have depths 340 that are defined similarly to the teeth 224 of FIG. 2, but are less than the depths 240 in FIG. 2. This decrease in tooth depth arises from the change in orientation of the concave medial curve 122; if the medial curve were flat, then the teeth would have the same depth along the medial curve.

The tooth gullet walls 326 and tooth undercuts 328 can be parallel to the tooth gullet walls 226 and tooth undercuts 228 of FIG. 2, respectively. The tooth lands 330 can be generally flat, can be generally parallel to the concave medial curve 122, and can extend generally along the concave medial curve 122. The gullets 332 between the teeth 324 can be convexly curved, with respective gullet radii 334. In some examples, the gullet radii 334 are equal to the gullet radii 234 of FIG. 2. In some examples, the pitches 338 and depths 340 of the distal series of teeth 324, in FIG. 3, are less than or are greater than the respective pitches 238 and depths 240 of the proximal series of teeth 224, in FIG. 2.

In some examples, the teeth 224, 324 and gullets 232, 332 are sized and shaped as a fraction of the pitch 238, 338. In some examples, each depth 240, 340 is 0.4 times the respective pitch 238, 338. In some examples, each tooth land 230, 330 has a length of 0.25 times the respective pitch 238, 338. In some examples, each gullet radius 234, 334 is 0.25 times the respective pitch 238, 338. Other suitable values may also be used.

In some examples, the posterior and/or anterior surfaces can include teeth with generally flat tooth lands, which can be shaped similar to the teeth shown in FIGS. 1-3. These teeth would provide the same advantages as the medial teeth, namely of reducing the probability of getting stuck by digging into hard medial bone, such as cortical bone, before the rasp has reached a proper alignment in the bones.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the inventors also contemplate examples in which only those elements shown or described are provided. Moreover, the inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, kit, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A surgical bone rasp, comprising:
   a body defining a longitudinal axis in a proximal-distal direction and having posterior, anterior, medial, and lateral surfaces,
   the medial surface including a distal straight portion and a proximal curved portion shaped to extend substantially along a concave medial curve,
   the proximal curved portion including a plurality of teeth, each tooth including a tooth gullet wall, a tooth undercut, and a generally flat tooth land between the tooth gullet wall and the tooth undercut, wherein for the teeth in the plurality, the tooth undercuts are equally spaced apart along the longitudinal axis,
   wherein the plurality of teeth have a plurality of pitches, oriented parallel to the concave medial curve, that increase gradually from a distal end of the proximal curved portion to a proximal end of the proximal curved portion.

2. The surgical bone rasp of claim 1, wherein for the teeth in the plurality, the tooth lands extend along the concave medial curve.

3. The surgical bone rasp of claim 1, wherein for the teeth in the plurality, the tooth gullet walls are parallel.

4. The surgical bone rasp of claim 3, wherein for the teeth in the plurality, the parallel tooth gullet walls are angled to extend away from the body between a distal direction and a medial direction.

5. The surgical bone rasp of claim 1, wherein for the teeth in the plurality, the tooth undercuts are parallel.

6. The surgical bone rasp of claim 5, wherein for the teeth in the plurality, the parallel tooth undercuts are angled to extend away from the body in a medial direction.

7. The surgical bone rasp of claim 1, wherein for the teeth in the plurality, the plurality of teeth have gullets therebetween, each gullet being concave with a gullet radius.

8. The surgical bone rasp of claim 7, wherein for the teeth in the plurality, the gullet radii are equal.

9. The surgical bone rasp of claim 1, wherein the plurality of teeth have a plurality of depths, oriented orthogonal to the concave medial curve, that increase from a distal end of the proximal curved portion to a proximal end of the proximal curved portion.

10. The surgical bone rasp of claim 1, wherein:
    each depth is 0.4 times the respective pitch;
    each land has a length of 0.25 times the respective pitch; and
    each gullet radius is 0.25 times the respective pitch.

11. The surgical bone rasp of claim 1, wherein the posterior and anterior surfaces of the body are flat.

12. A surgical bone rasp, comprising:
    a body defining a longitudinal axis in a proximal-distal direction and having posterior, anterior, medial, and lateral surfaces,
    the medial surface including a distal straight portion devoid of teeth and a proximal curved portion shaped to extend substantially along a concave medial curve,
    the proximal curved portion including a plurality of teeth, each tooth including a tooth gullet wall, a tooth undercut, and a tooth land between the proximal and tooth undercuts,
    wherein the plurality of teeth have a plurality of depths, oriented orthogonal to the concave medial curve, that increase gradually from a distal end of the proximal curved portion to a proximal end of the proximal curved portion, and
    wherein, for the plurality of teeth:
    the tooth gullet walls are parallel to one another and are angled to extend away from the body between a distal direction and a medial direction,
    the tooth lands are generally flat and extend along the concave medial curve, and
    the tooth undercuts are parallel to one another, are angled to extend away from the body in a medial direction, and are equally spaced apart along the longitudinal axis.

13. The surgical bone rasp of claim 12, wherein for the teeth in the plurality, the plurality of teeth have gullets therebetween, each gullet being concave with a gullet radius.

14. The surgical bone rasp of claim 13, wherein for the teeth in the plurality, the gullet radii are equal.

15. The surgical bone rasp of claim 12, wherein the posterior and anterior surfaces of the body are flat.

16. A surgical bone rasp, comprising:
    a body defining a longitudinal axis in a proximal-distal direction and having posterior, anterior, medial, and lateral surfaces,
    the medial surface including a distal straight portion and a proximal curved portion shaped to extend substantially along a concave medial curve, the proximal curved portion including a plurality of teeth, each tooth including a tooth gullet wall, a tooth undercut, and a generally flat tooth land between the tooth gullet wall and the tooth undercut, wherein for the teeth in the plurality, the tooth undercuts are equally spaced apart along the longitudinal axis, wherein the plurality of teeth have a plurality of depths, oriented orthogonal to the concave medial curve, that increase gradually from a distal end of the proximal curved portion to a proximal end of the proximal curved portion to maintain the equal spacing of the tooth undercuts as an orientation of the concave medial curve changes.

17. The surgical bone rasp of claim 16, wherein the surgical bone rasp is symmetrical about a coronal plane.

* * * * *